United States Patent [19]

Mehl et al.

[11] Patent Number: 4,886,071

[45] Date of Patent: * Dec. 12, 1989

[54] PACKAGE INCLUDING SYRINGE AND NEEDLE

[75] Inventors: Jack J. Mehl, Landing; Raymond T. Wasek, East Rutherford; Jay Desai, Closter, all of N.J.

[73] Assignee: Becton, Dickinson and Company, Franklin Lakes, N.J.

[*] Notice: The portion of the term of this patent subsequent to May 19, 2004 has been disclaimed.

[21] Appl. No.: 20,630

[22] Filed: Mar. 2, 1987

Related U.S. Application Data

[62] Division of Ser. No. 546,674, Oct. 28, 1983, Pat. No. 4,666,850.

[51] Int. Cl.$^4$ .............................................. A61B 5/00
[52] U.S. Cl. .................................. 128/760; 206/366; 206/569
[58] Field of Search ...................... 128/763, 770, 760; 604/51, 189, 264, 272, 403; 206/363–366, 569–571

[56] References Cited

U.S. PATENT DOCUMENTS

| | | | |
|---|---|---|---|
| 1,625,035 | 4/1927 | Lilly | 206/571 |
| 2,755,920 | 7/1956 | Werkman | 206/366 |
| 2,836,942 | 6/1958 | Miskel | 206/365 |
| 3,013,656 | 12/1961 | Murphy | 206/569 |
| 3,074,540 | 1/1963 | Beich et al. | 206/366 |
| 3,207,302 | 9/1965 | Hobbs | 206/366 |
| 3,505,889 | 12/1966 | Vanderbeck | 206/365 |
| 4,122,947 | 10/1978 | Falla | 206/569 |
| 4,166,533 | 9/1979 | Maitland | 206/366 |
| 4,184,593 | 1/1980 | Dorr | 206/365 |
| 4,398,544 | 8/1983 | Nugent et al. | 128/763 |

FOREIGN PATENT DOCUMENTS

| | | | |
|---|---|---|---|
| 866614 | 3/1971 | Canada | 206/365 |
| 824985 | 2/1938 | France | 206/366 |
| 705205 | 3/1954 | United Kingdom | 206/366 |
| 1144837 | 3/1969 | United Kingdom | 206/365 |

Primary Examiner—Max Hindenburg
Attorney, Agent, or Firm—Robert P. Grindle

[57] ABSTRACT

A system is provided for receiving, maintaining and processing blood samples for the subsequent separation and testing thereof. A pre-packaged blood sample receiving vessel is provided containing appropraite additives and a quantity of beads or other physical bodies for subsequent lysis, centrifugation, and separation of the sample. An additional pre-packaged arrangement is provided at the lab for the handling and removal of the lysed, centrifuged and separated sample in order to obtain the desired portion of the sample for appropriate laboratory testing procedures.

1 Claim, 2 Drawing Sheets

PACKAGE INCLUDING SYRINGE AND NEEDLE

This is a division of application Ser. No. 546,674, filed Oct. 28, 1983, now U.S. Pat. No. 4,666,850.

BACKGROUND AND STATEMENT OF THE INVENTION

Generally speaking, this invention relates to processes and apparatus for receiving blood samples for the subsequent testing of the components thereof. More particularly, this invention relates to processes and devices for the recovery of bacteria from blood by lysis and centrifugation.

Concentration of organisms by centrifugation has been well known for a number of years, such as Mycobacterium from sputum, and the obtaining of bacteria from spinal fluids, and so forth. In recent years, developments have been made of specific devices for receiving and processing blood samples, which devices are configured in such a way and contain certain components for the subsequent lysis and separation of the components of the blood sample by centrifugation. Representative of these recent developments are U.S. Pat. Nos. 4,164,449; 4,131,512 and 3,883,435.

These developments include using purified saponin, detoxified by either gel filtration or passing through a filter, in order to obtain a specific pore size through ultrafiltration. The procedures taught in these patents include testing for toxicity of saponin prior to its introduction into the devices for the subsequent lysis and separation procedures. Representative of other arrangements involved in these patents include the use of a liquid cushioning agent and an angled surface positioned in the separation device in order to provide appropriate separation of the various components of the sample, once centrifugation has taken place.

Difficulties may arise in the use of the arrangements as taught in these patents, including a double-ended tube for the introduction and removal of components from the tube, in that the layers are separated only by liquid cushioning agent type procedures and so forth. Thus, control of the removal of the supernatant is difficult due to the necessary manipulation, or accidental refluxing by the user, causing further dilution and potential loss of organisms prior to the actual separation of the layers in the devices. In most instances, the double-ended tube is required.

With this invention, by contrast, a device is provided for receiving blood samples, which device includes certain components in combination with physical beads or cylinders configured to prevent disturbing the sediment following centrifugation, and during withdrawal of the supernatant. Removal of the supernate using a pre-packaged arrangement, in accordance herewith, provides simple removal of the supernatant from the centrifuged sample with fewer manipulations. Also, prior detoxification and filtering of the saponin in the receiving container is not required.

In addition, the arrangement herein contains a combination of certain nutrients which facilitate the growth of organisms in the event of a delay in the processing of the sample. The sample may be maintained over a period of time between the time the sample is taken and the time when it is actually conveyed to a laboratory for testing, thus, removing the danger of the organisms to be tested having been destroyed by the contents of the container over a period of time prior to any testing thereof.

Thus, the invention herein includes a prepackaged evacuated container containing non-purified and non-detoxified saponin. This may be obtained from conventional sources such as, for example, practical grade saponin from Eastman Chemical Company or Fisher Scientific Company. While it is appropriate, as will be understood by practitioners-in-the-art, to pretest saponin prior to its introduction into the evacuated container because batches of saponin will vary, it is not necessary to purify, filter or detoxify the saponin prior to its introduction. The inventors have discovered, also, that by including certain other additives or nutrients in the device of the invention, the growth of organisms is facilitated in the event of a delay in processing the sample. Such materials, as discussed in more detail below, include, for example, yeast extract or other peptones, amino acids and co-enzymes.

Also included in the container are particles in the form of beads, pellets or cylinders which serve to enhance the separation during centrifugation of the components of the sample to be rested. Due to the solid or physical properties of the beads or other configured particles introduced into the evacuated tube for receiving the sample, there is less opportunity for the user to disturb the microbial sediment or concentrate during transfer of the specimen from the centrifuge to the work area.

The invention here includes, in addition to the prepackaged evacuated container for receiving the blood sample, a pre-packaged supernate and sediment removal unit for use by the laboratory in obtaining the appropriate separated components of the sample once lysis and centrifugation have taken place. The pre-packaged arrangement includes a supernate transfer needle for penetration of the evacuated container containing the sample. This needle may be used once centrifugation has taken place for withdrawing the supernate from the original sample receiving container. The package also includes a vent needle which is inserted prior to the removal of the supernate in order to facilitate this removal. In addition, the package includes an evacuated sterile container for receiving the supernate. Finally, the package includes a needle and syringe for removing aliquots of the remaining concentrate in the original sample containing container for distribution on appropriate culture plates.

Thus, as purely illustrative of a procedure which may be utilized, in accordance with this invention, first blood is collected from a patient by drawing directly into an evacuated pre-packaged container The pre-packaged container contains a specific formulation for enhancing the maintenance of the sample during a period prior to the sample being received and processed in the laboratory. Subsequently, on arrival in the laboratory, the sample is centrifuged. A representative centrifuging process would be at 3000-3500XG for 30-45 minutes.

Subsequently, the top of the stopper of the centrifuged container is disinfected and the vent needle from the separate packaging, in accordance herewith, is introduced into the stopper. Then the supernate transfer needle is made to penetrate the stopper. It will be understood that the needle is of a sufficient length to be introduced into the container to the level of the beads or cylinders or other material utilized for the physical separation procedure. A second evacuated container, which is sterile, is removed from this package. This evacuated container will have sufficient vacuum to draw nine to ten milliliters from the original centrifuged container.

After the supernate is withdrawn, the supernate tube and transfer needle are removed. However, the vent needle is left in place. The tube containing the supernate, as will be understood, may be removed from the transfer unit and stored. The tube containing the beads or cylinders and microbial concentrate is then vortexed. Subsequent to this procedure, the tube is inverted and the beads are tapped to the stopper end along with the solution of concentrate. Then, utilizing the needle and syringe from the very same package, the sample is removed and aliquots of the concentrate are distributed, as mentioned above, on appropriate culture plates.

As stated above, one of the significant aspects of this invention is the introduction in the sample receiving container of a component which maintains and facilitates growth of microorganisms, when present in the sample prior to its being received and worked upon by a laboratory. Representative formulations include, for example, a yeast extract present within the range of between about 0.5-3 grams, and preferably 1 gram, sodium polyanethole sulfonate present within the range of between about 0.8-1.5 grams and preferably 1 gram, a practical grade non-purified and non-detoxified saponin present within the range of between about 10 and 15 grams, and, preferably, 10 grams, and IsoVitaleX TM, a product of BBL Laboratories, Division of Becton Dickinson and Company, Baltimore, Maryland, present within the range of between about 1-3 milliliters, and preferably one milliliter, with the above four components dissolved in 100 milliliters of water. The IsoVitaleX TM is a nutrient component containing nicotinamide adenine dinucleotide, glutamine, vitamin $B_{12}$, and a sulfur containing amino acid such as cysteine. Added to the above formulation is sufficient sodium bicarbonate to adjust the pH to between 6.9 and 7.4.

As further illustrative of components which may be added to the evacuated container the formulation above may have added to it Rhozyme ® proteases within the range of between about 0.4 gram, and preferably 5 gram. The Rhozyme ® proteases usually selected will be Rhozyme 41® concentrate, a product of Rhome and Haas, and which is a proteolytic agent.

Representative formulations for addition to an evacuated container, containing the beads or cylinders, for subsequent lysing and centrifugation are listed below.

| FORMULA 1 | |
|---|---|
| 1 gram | yeast extract |
| 1 gram | sodium polyanethole sulfonate |
| 10 grams | saponin-practical grade- non detoxified |
| 1 milliliter | IsoVitalex TM |

The above four components are dissolved in 100 milliliters of water and approximately 1.6 grams of sodium bicarbonate is added to adjust the pH to within the range of between about 6.9 and 7.4.

| FORMULA 2 | |
|---|---|
| 1 gram | yeast extract |
| 1 gram | sodium polyanethole sulfonate |
| 1 milliliter | IsoVitaleX TM |
| 10 grams | saponin |
| 0.5 grams | Rhozyme 41 ® |

The above five components are dissolved in 100 milliliters of water and sufficient sodium bicarbonate is added to adjust the pH to within the range of 6.9 to 7.4.

With respect to the beads or cylinders or other small objects introduced into the evacuated container for receiving the sample initially, the beads or cylinders may be comprised of plastic or a glass material, and they must be selected to be of a size which does not pack and restrict the sedimentation of bacteria at the bottom of the tube during centrifugation. Examples of satisfactory materials are cylinders having a length within the range of between about 3 and 5 mm. and a diameter within the range of between about 2 and 3 millimeters. Beads may have a representative dimension within the range of between 2 and 5 mm. in diameter. Representative materials include polycarbonate such as Lexan, a product of General Electric Company, or polytetrafluoroethylene.

Other objects and advantages of this invention will be apparent from the following description, the accompanying drawings and the appended claims.

DETAILED DESCRIPTION OF THE INVENTION

Figure 1:
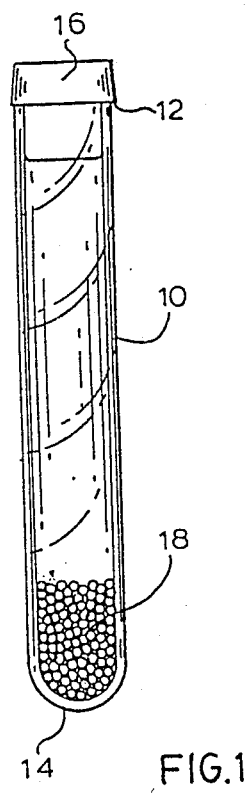
FIG. 1 is a longitudinal sectional view of an evacuated container for use as the concentration system of the invention.

Referring to the drawings in which like reference characters refer to like parts throughout the several views thereof, FIG. 1 shows the concentration system of the invention which is in the form of an evacuated container for receiving initially the blood sample. The evacuated container 10 is in the form of an elongated tube having an open end 12 and a closed end 14. Introduced into the pre-packaged evacuated container, prior to evacuation thereof is a representative quantity of particles 18, which may be beads or cylinders as discussed above, for the subsequent separation procedures once a blood sample is introduced into the container. Also introduced into the container is the representative Formula 1 or Formula 2 as noted above. The evacuated container size may vary depending upon the amount of additive, as long as the total additives content are generally in the ratio of 1 part additive to 18–20 parts blood specimen. Thus, an evacuated tube will contain about 0.5 ml. additive to draw 9.5–10 ml. of blood specimen. The actual quantity of beads, or cylinders introduced into the container will be within the range of between about 1 gram and 3 grams, depending upon the material used. The column height of the particles or beads should be between 1 and 2 inches.

Once the formula for maintaining the sample has been introduced into the container and the particles 18 introduced, the tube is then sealed with a conventional evacuated tube stopper 16 and, during the introduction of the stopper the evacuation procedure is applied to the tube so that it is properly evacuated. This concentration system is pre-packaged for use by the medical practitioner or paramedic in taking a blood sample. Once the sample is introduced for the subsequent procedures, as discussed above, wherein tube 10 is centrifuged for a period of time and at a specific rate, as desired.

Figure 2:
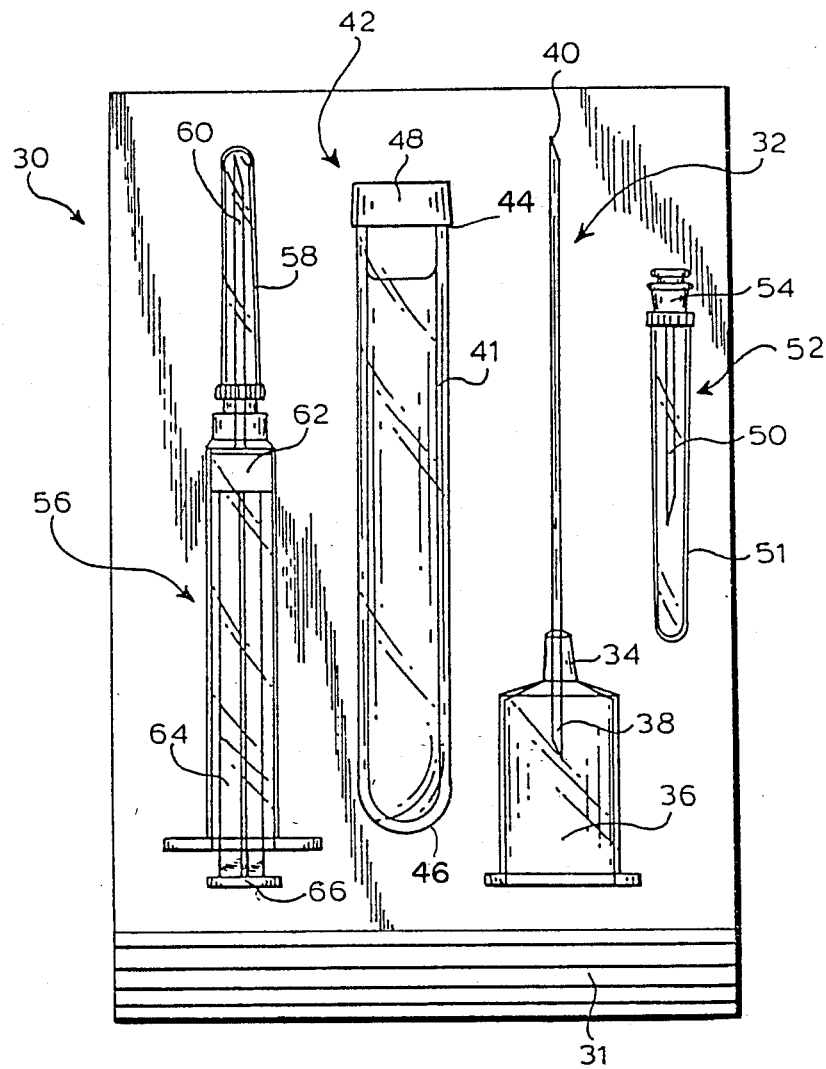
FIG. 2 is a perspective view of a second prepackaged portion of the system of the invention for use in the laboratory.

Referring now to FIG. 2, a pre-packaged arrangement is provided in the laboratory in the form of a centrifugation system for detecting bacteremia. This package is the supernate and sediment removal units all in a single container for the technician to utilize once the initial evacuated container, as shown and described in FIG. 1 has been centrifuged. Thus, the evacuated container stopper 16 is disinfected, probably with iodine, and the vent needle 50 on holder 54 is removed from its shield 51. The vent needle 50 is then inserted in stopper 16.

Subsequent to this insertion, the supernate transfer needle 32, mounted on tube holder 36 has the point 40 thereof inserted into and through stopper 16 to the level of the beads 18 in tube 10. Then the evacuated tube 41, having an open end 44 and a closed end 46, with a stopper 48 closing the open end 44, is inserted into holder 36 so that the point 38 of needle 32 will penetrate through stopper 48.

Tube 41, as will be understood, has sufficient volume to draw 9-10 milliliters of the supernate from tube 10. It should be pointed out in this respect, that tube 10 may simply be placed in a tube rack for the removal of the supernatant material therefrom. It is not necessary for the tube to be held at a specific angle for the removal of the supernatant, as required in prior art procedures. Moreover, because the tube may be placed in a tube rack, it does not have to be maintained at eye level for this removal, thus allowing for batch procedures, rather than specific handling of each individual tube for the removal of the supernatant component contained in the tube. This stabilized procedure also provides for a constant volume removal of supernatant from evacuated tube 10, thus minimizing the chance of erroneous results. The user avoids other manipulation procedures which may cause accidental refluxing partially removing supernatants back into the concentrated organism during this separation procedure.

Once the supernatant has been removed, the vent needle is left in place, and the tube 41, containing the supernate may be removed from the transfer unit and stored. Tube 10, containing the particles 18, as discussed previously, and the remaining microbial concentrate are vortexed. Thereafter, tube 10 is inverted and the beads are tapped to the stopper end along with the solution of the concentrate. Then, the syringe and needle apparatus 56 in package 30 may be utilized to remove through stopper 16 the concentrate. Thus, shield 58 is removed from needle 60 of the syringe and needle unit 56, and the handle 66 is utilized to draw plunger 62 to remove the concentrate from tube 10 through stopper 16. Aliquots of this concentrate contained in syringe 56 may then be distributed on appropriate culture plates, as desired. It will be noted in FIG. 2, that the package 30 is sealed in the usual sterile package arrangement which may be pealed open at 31, as desired. It will be understood, that package 30 is desirably comprised of a flexible clear plastic material so that contents thereof are clearly visible for the technician.

As discussed previously in this specification, the particular system, in accordance herewith, utilizes an additive introduced into evacuated container 10 for receiving the initial sample. This additive has the effect of maintaining the sample in appropriate condition for a relatively long period from the time the sample is received in the container until such time as the laboratory has time to work upon the sample. As will be appreciated, this is a necessary provision because many doctors take samples from their patients in the office and a certain amount of time is taken from receipt of the sample until such time as the laboratory technician has an opportunity to lyse and centrifuge the sample for subsequent procedures. Thus, it is helpful if the sample may be maintained for as long as 18 to 24 hours without having a deleterious effect upon the organisms contained in the sample. A representative comparison was made utilizing the invention herein containing Formula 2 and three different organisms were tested. As a comparison, an ISOLATOR TM brand unit was tested also. The ISOLATOR TM brand unit is configured in accordance with the teachings of the patents noted above in this specification. Table 1 below shows the comparisons made during this test procedure.

TABLE I

| Organisms | Unit tested | Unit held 18-24 hours before centrifugation at 35° C. | | | | |
|---|---|---|---|---|---|---|
| | | "o" time | | | 24 hours | |
| | | CFU/tube | x̄ | CFU | Supernatant | Sediment |
| L. monocytogenes | A | 595 | | ±87.8 | tntc | CF |
| | B | 595 | | | 0 | 0 |
| S. pneumoniae | A | 13 | | ±4 | tntc | CF |
| | B | 13 | | | 0 | 0 |
| S. pyogenes | A | 126 | | ±8.4 | tntc | CF |
| | B | 126 | | | 0 | 0 | x̄ = average of 5 plates: 0.3 ml/plate
CF = confluent growth (>1000 CFU)
SD = Standard Deviation
tntc = too numerous to count on plate (>500 CFU)
CFU = Colony Forming Units
A - Unit according to invention
B - Dupont Brand ISOLATOR TM Unit As can be seen in Table 1, organisms were destroyed using the ISOLATOR TM brand unit after a 24-hour period while the organisms were maintained stabilized for subsequent testing with the unit of the invention, in accordance herewith. Indeed, each of the three organisms compared, were too numerous to count on the plate and having greater than 500 colony forming units at least in the supernatant, and having confluent growth of greater than 1000 colony forming units in the sediment.

Thus, as will be appreciated, there is provided in accordance with this invention a system and a procedure for receiving a blood sample containing bacteria which system provides for the subsequent lysis and centrifugation of the blood sample to obtain the desired bacteria for subsequent testing. The system includes a formula for maintaining the sample over a long period of time between the time the sample is taken, and the time the laboratory technician has time to obtain the sample and to make appropriate processing procedures to the sample in order to obtain the desired number of culture plates of the bacteria contained. Moreover, the process and package of the invention includes a complete sterile package of components all necessary for carrying out the procedure for separating and removing the supernatant and concentrated components of the blood sample, once the sample has been received by the laboratory technician for centrifugation. As will be appreciated, the arrangement is such that the samples are in appropriate condition for proper testing with sufficient bacteria to carry out the proper testing procedures.

While the systems and methods herein described constitute preferred embodiments of this invention, it is to be understood that this invention is not limited to these precise methods and systems of apparatus, and that changes may be made therein without departing from the scope of the invention which is defined in the appended claims.

What is claimed is:

1. A package for separating and handling the supernate and concentrate portions of a lysed and centrifuged blood sample held in an evacuated tube, characterized by
    (a) a sealed sterile flexible pouch;
    (b) an evacuated tube holder in said pouch;
    (c) a supernate transfer needle mounted on and extending through said evacuated tube holder for withdrawing the supernate portion of the said lysed and centrifuged blood sample held in an evacuated tube;
    (d) said supernate transfer needle being pointed at both ends and having a long end for penetration into an evacuated tube holding said lysed and centrigued blood sample, and a short end extending into said tube holder;
    (e) an evacuated tube in said pouch for insertion into said tube holder, and having a stopper for penetration by said short end for receiving the said supernate portion from an evacuated tube holding said lysed and centrifuged blood sample;
    (f) a plugged vent needle in said pouch for venting the stopper of a sample containing evacuated tube holding said lysed and centrifuged blood sample during removal of the contents thereof; and
    (g) a syringe and needle in said pouch for removing a concentrate portion from said lysed and centrifuged blood sample containing evacuated tube.

* * * * *